United States Patent [19]
Greenlee et al.

[11] Patent Number: 6,040,448
[45] Date of Patent: Mar. 21, 2000

[54] CERTAIN 1-(2-NAPHTHYL) AND 1-(2-AZANAPHTHYL)-4-(1-PHENYLMETHYL) PIPERAZINES, DOPAMINE RECEPTOR SUBTYPE SPECIFIC LIGANDS

[75] Inventors: William Greenlee, Teaneck; Ashit Gangly, U. Montclair, both of N.J.; Jan W. F. Wasley, Guilford, Conn.

[73] Assignee: Neurogen Corporation, Branford, Conn.

[21] Appl. No.: 09/177,956

[22] Filed: Oct. 23, 1998

Related U.S. Application Data

[60] Provisional application No. 60/063,149, Oct. 24, 1997.

[51] Int. Cl.$^7$ .................................................. C07D 403/04
[52] U.S. Cl. .......................... 544/363; 544/292; 544/353; 544/356; 544/392; 544/394
[58] Field of Search ............................................ 544/363

[56] References Cited

U.S. PATENT DOCUMENTS

| | | | |
|---|---|---|---|
| 3,808,212 | 4/1974 | Renth et al. .............................. | 544/377 |
| 3,917,597 | 11/1975 | Regnier et al. .......................... | 544/295 |
| 3,944,551 | 3/1976 | Regnier et al. .......................... | 544/363 |
| 4,831,031 | 5/1989 | Lowe, III et al. ....................... | 514/254 |
| 5,206,366 | 4/1993 | Bowles ..................................... | 544/363 |
| 5,945,421 | 8/1999 | Belliotti et al. .......................... | 514/253 |

FOREIGN PATENT DOCUMENTS

97/39748  10/1997  WIPO .

OTHER PUBLICATIONS

Terron et al. Arch.Med. Res., 25 (4), p. 435–440, 1994.
Terron et al. *Chemical Abstracts*, vol. 122, No. 204541, 1995.

*Primary Examiner*—Emily Bernhardt
*Attorney, Agent, or Firm*—McDonnell Boehnen Hulbert & Berghoff

[57] ABSTRACT

Disclosed are compounds of the formula:

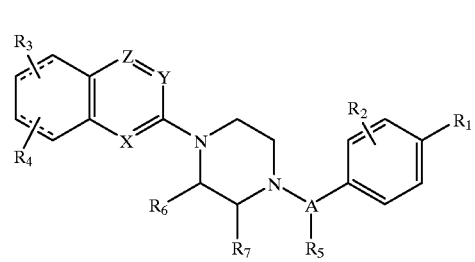

or pharmaceutically acceptable addition salts thereof, wherein:

X, Y and Z are the same or different and represent optionally substituted carbon or nitrogen;

$R_1$ and $R_2$ independently represent organic or inorganic substituents;

$R_3$ and $R_4$ are variables independently representing inorganic or organic substituents;

A represents $C_1$–$C_4$ alkylene; and $R_5$, $R_6$, and $R_7$ independently represent hydrogen or $C_1$–$C_6$ alkyl, which compounds bind selectively with high affinity to the dopamine $D_4$ receptor subtype and are therefore of use in treatment of various neuropsychological disorders.

23 Claims, No Drawings

CERTAIN 1-(2-NAPHTHYL) AND 1-(2-AZANAPHTHYL)-4-(1-PHENYLMETHYL) PIPERAZINES, DOPAMINE RECEPTOR SUBTYPE SPECIFIC LIGANDS

This application claims the benefit of U.S. provisional application Ser. No. 60/063,149, filed Oct. 24, 1997.

BACKGROUND OF THE INVENTION

1. Field of the Invention

This invention relates to certain 1-(2-naphthyl) and 1-(2-azanaphthyl)-4-(1-phenylmethyl)piperazines and pharmaceutical compositions containing such compounds. It also relates to the use of such compounds in the treatment or prevention of psychotic disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has recently been identified (Nature, 347: 146 (Sokoloff et al., 1990)). Its unique localization in limbic brain areas and its differential recognition of various antipsychotics suggest that the $D_4$ receptor may play a major role in the etiology of schizophrenia. Selective $D_4$ antagonists are considered effective antipsychotics free from the neurological side effects displayed by conventional neuroleptics.

Various 4-benzylpiperazines have been described. See, for example, Arch. Med. Res., 25: 435–440 (Terron et al., 1994) and Toxicol. Appl. Pharmacol., 7: 257–267 (Schmidt and Martin, 1965).

SUMMARY OF THE INVENTION

This invention provides novel compounds which interact with dopamine subtypes. Accordingly, in a broad aspect, the invention provides compounds of Formula I:

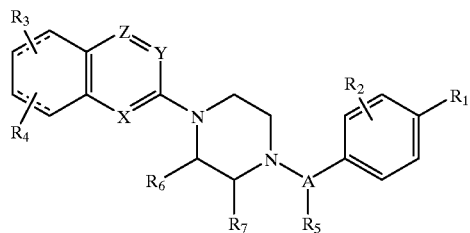

I or pharmaceutically acceptable addition salts thereof, wherein:

- X, Y and Z are the same or different and represent $CR_c$ or nitrogen;
- $R_c$ represents hydrogen, halogen or $C_1$–$C_6$ alkyl;
- $R_1$ and $R_2$ independently represent hydrogen, halogen, hydroxy, $C_1$–$C_6$ alkyl, trifluoromethyl, trifluoromethoxy or $SO_2NH_2$, provided that, when Y and Z represent CH, and $R_3$ and $R_4$ are both hydrogen, $R_1$ and $R_2$ are not hydrogen simultaneously; or
- $R_1$ and $R_2$ together represent a $C_1$–$C_2$ alkylene dioxy group or a $C_1$–$C_3$ alkylene oxy group;
- $R_3$ and $R_4$ are the same or different and represent hydrogen, halogen, $C_1$–$C_6$ alkyl, $C_1$–$C_4$ alkoxy, alkylthio, hydroxy, amino, mono or dialkyl amino where each alkyl is $C_1$–$C_6$ alkyl, cyano or trifluoromethyl;
- A represents $C_1$–$C_4$ alkylene; and $R_5$, $R_6$, and $R_7$ independently represent hydrogen or $C_1$–$C_6$ alkyl.

Dopamine $D_4$ receptors are concentrated in the limbic system (Science, 265: 1034 (Taubes, 1994)) which controls cognition and emotion. Therefore, compounds that interact with these receptors are useful in the treatment of cognitive disorders. Such disorders include cognitive deficits which are a significant component of the negative symptoms (social withdrawal and unresponsiveness) of schizophrenia. Other disorders include those involving memory impairment or attention deficit disorders.

Compounds of the present invention demonstrate high affinity and selectivity in binding to the $D_4$ receptor subtype. These compounds are therefore useful in treatment of a variety of neurospychological disorders, such as, for example, schizophrenia, psychotic depression and mania. Other dopamine-mediated diseases such as Parkinsonism and tardive dyskinesias can also be treated directly or indirectly by modulation of $D_4$ receptors.

Thus, in another aspect, the invention provides methods for treatment and/or prevention of neuropsychochological or affective disorders including, for example, schizophrenia, mania, dementia, depression, anxiety, compulsive behavior, substance abuse, memory impairment, cognitive deficits, Parkinson-like motor disorders, e.g., Parkinsonism and dystonia, and motion disorders related to the use of neuroleptic agents. In addition, the compounds of the invention are useful in treatment of depression, memory-impairment or Alzheimer's disease by modulation of $D_4$ receptors which selectively exist in limbic area known to control emotion and cognitive functions. Further, the compounds of the present invention are useful for the treatment of other disorders that respond to dopaminergic blockade, e.g., substance abuse and obsessive compulsive disorder. These compounds are also useful in treating the extrapyramidal side effects associated with the use of conventional neuroleptic agents.

In yet another aspect, the invention provides pharmaceutical compositions comprising compounds of Formula I.

DETAILED DESCRIPTION OF THE INVENTION

As mentioned above, the invention encompasses substituted 1-(2-naphthyl) and 1-(2-azanaphthyl)-4-(1-phenylmethyl)piperazines of Formula I. Preferred compounds of Formula I are those where at least one of $R_1$ and $R_2$ is halogen, alkyl, trifluoromethyl, trifluoromethoxy, or where $R_1$ and $R_2$ together represent 3,4-methylenedioxy. Still other preferred compounds of Formula I are those where

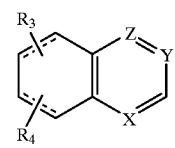

represents 4-alkylquinolinyl, 4,6-dialkylquinolinyl, 4,7-dialkylquinolinyl, 4,8-dialkylquinolinyl, 4-haloquinolinyl, or 4-alkyl-6-alkoxyquinolinyl. Preferably, only Z is $R_c$. More preferred compounds of Formula I are those where at least one of $R_1$ and $R_2$ is chloro, fluoro, methyl, ethyl, butyl, isopropyl, n-propyl, trifluoromethyl, trifluoromethoxy, or where $R_1$ and $R_2$ together represent 3,4-methylenedioxy. Particularly preferred compounds of Formula I are those where $R_2$ is hydrogen and $R_1$ is methyl or chloro. In addition, preferred compounds of Formula I are those where A is methylene or ethylene, and $R_5$ is hydrogen.

Particularly preferred compounds of Formula I are those where

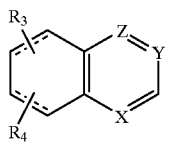

represents quinolin-2-yl, 5,6,7,8-tetrahydroquinolin-2-yl, quinoxalin-2-yl, or naphth-2-yl.

The invention also encompasses compounds of formula II:

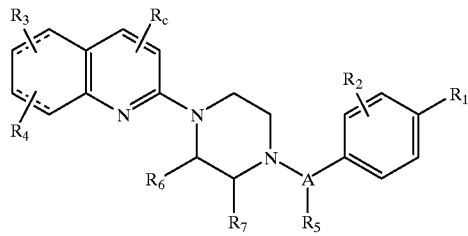

wherein:

$R_1$, $R_2$, $R_3$, $R_4$, $R_5$, $R_6$, $R_c$, and $R_7$ carry the same definitions as set forth above for Formula I.

Preferred compounds of Formula II are those where at least one of $R_1$ and $R_2$ is halogen, alkyl, trifluoromethyl, trifluoromethoxy, or where $R_1$ and $R_2$ together represent 3,4-methylenedioxy. Still other preferred compounds of Formula II are those where the both $R_3$ and $R_4$ are hydrogen, or the $R_c$, $R_3$ and $R_4$ substitution on the quinoline ring provides a 4-alkylquinolinyl, 4,6-dialkylquinolinyl, 4,7-dialkylquinolinyl, 4,8-dialkylquinolinyl, 4-haloquinolinyl, or 4-alkyl- 6-alkoxyquinolinyl compound. More preferred compounds of Formula II are those where A is methylene and at least one of $R_1$ and $R_2$ is chloro, fluoro, methyl, ethyl, butyl, isopropyl, n-propyl, trifluoromethyl, trifluoromethoxy, or where $R_1$ and $R_2$ together represent 3,4-methylenedioxy. Particularly preferred compounds of Formula II are those where $R_3$ and $R_4$ are hydrogen, A is methylene, $R_2$ is hydrogen and $R_1$ is methyl or chloro.

Particularly preferred compounds of Formula II are quinolin-2-yl derivatives where $R_3$ and $R_4$ are hydrogen. Other particularly preferred compounds of Formula II are 5,6,7,8tetrahydroquinolin-2-yl derivatives where $R_3$ and $R_4$ are hydrogen.

Also encompassed within the invention are compounds of Formula III:

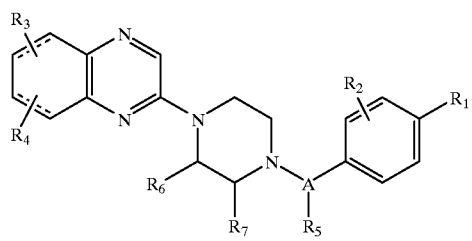

wherein:

$R_1$, $R_2$, $R_3$, $R_4$, $R_5$, $R_6$, and $R_7$ carry the same definitions as set forth above for Formula I.

Preferred compounds of Formula III are those where at least one of $R_1$ and $R_2$ is halogen, alkyl, trifluoromethyl, trifluoromethoxy, or where $R_1$ and $R_2$ together represent 3,4-methylenedioxy. More preferred compounds of Formula III are those where A is methylene and at least one of $R_1$ and $R_2$ is chloro, fluoro, methyl, ethyl, butyl, isopropyl, n-propyl, trifluoromethyl, trifluoromethoxy, or where $R_1$ and $R_2$ together represent 3,4-methylenedioxy. Particularly preferred compounds of Formula III are those where $R_3$ and $R_4$ are hydrogen, A is methylene, $R_2$ is hydrogen and $R_1$ is methyl or chloro.

Particularly preferred compounds of Formula III are quinoxalin-2-yl derivatives where $R_3$ and $R_4$ are hydrogen.

The invention further provides compounds of formula IV:

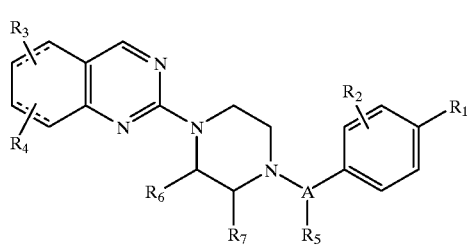

wherein:

$R_1$, $R_2$, $R_3$, $R_4$, $R_5$, $R_6$, and $R_7$ carry the same definitions as set forth above for Formula I.

Preferred compounds of Formula IV are those where at least one of $R_1$ and $R_2$ is halogen, alkyl, trifluoromethyl, trifluoromethoxy, or where $R_1$ and $R_2$ together represent 3,4-methylenedioxy. More preferred compounds of Formula IV are those where A is methylene and at least one of $R_1$ and $R_2$ is chloro, fluoro, methyl, ethyl, butyl, isopropyl, n-propyl, trifluoromethyl, trifluoromethoxy, or where $R_1$ and $R_2$ together represent 3,4-methylenedioxy. Particularly preferred compounds of Formula IV are those where $R_3$ and $R_4$ are hydrogen, A is methylene, $R_2$ is hydrogen and $R_1$ is methyl or chloro.

The invention also encompasses compounds of formula V:

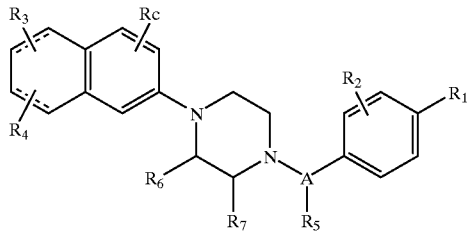

wherein:

$R_1$, $R_2$, $R_3$, $R_4$, $R_5$, $R_6$, $R_c$, and $R_7$ carry the same definitions as set forth above for Formula I.

Preferred compounds of Formula V are those where $R_c$ is hydrogen; and at least one of $R_1$ and $R_2$ is halogen, alkyl, trifluoromethyl, trifluoromethoxy, or where $R_1$ and $R_2$ together represent 3,4-methylenedioxy. More preferred compounds of Formula V are those where $R_c$ is hydrogen, A is methylene and at least one of $R_1$ and $R_2$ is chloro, fluoro, methyl, ethyl, butyl, isopropyl, n-propyl, trifluoromethyl, trifluoromethoxy, or where $R_1$ and $R_2$ together represent 3,4-methylenedioxy. Particularly preferred compounds of Formula V are those where $R_3$ and $R_4$ are hydrogen, A is methylene, $R_2$ is hydrogen and $R_1$ is methyl or chloro.

The particularly preferred compounds of Formula V are naphth-2-yl derivatives where $R_3$ and $R_4$ are hydrogen.

Particularly preferred compounds of Formulae I-V are those where $R_5$, $R_6$, and $R_7$ are hydrogen.

The invention further provides intermediates useful in the preparation of compounds of Formula I. Such intermediates include those of Formula VIII.

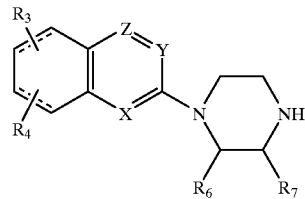

VIII where X, Y, Z, $R_3$, $R_4$, and $R_6$ and $R_7$ are as defined above for Formula I.

In certain situations, the compounds of this invention I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n-ACOOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By the use herein of dashed lines in the structural representations of the compounds of the invention is meant that the carbon atoms connected by the dashed line are linked either by single or double carbon-carbon bonds.

The use herein of the following structure

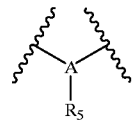

where A represents $C_1$–$C_4$ alkylene and $R_5$ is hydrogen or lower alkyl ("the AR$_5$ group"), means alkylene groups having from 1–4 carbon atoms each of which carbon atoms is optionally substituted with a lower alkyl group. Examples of such a structure are methylene, ethylene, propylene, and butylene. A particularly preferred AR$_5$ group according to the invention is methylene, i.e., —CH$_2$—.

By alkyl or lower alkyl in the present invention is meant $C_1$–$C_6$ alkyl, i.e., straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By alkoxy or lower alkoxy in the present invention is meant $C_1$–$C_6$ alkoxy, i.e., straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By cycloalkoxy in the present invention is meant cycloalkylalkoxy groups having 3–7 carbon atoms where cycloalkyl is defined above.

By $C_1$–$C_2$ alkylene dioxy group is meant a group of the formula:

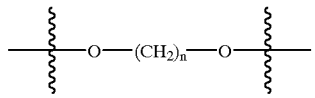

where n is 1 or 2.

By $C_1$–$C_3$ alkylene oxy group is meant a group of the formula:

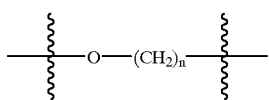

where n is 1, 2 or 3.

By halogen in the present invention is meant fluorine, bromine, chlorine, and iodine.

Representative compounds of the invention are shown below in Table 1.

TABLE 1

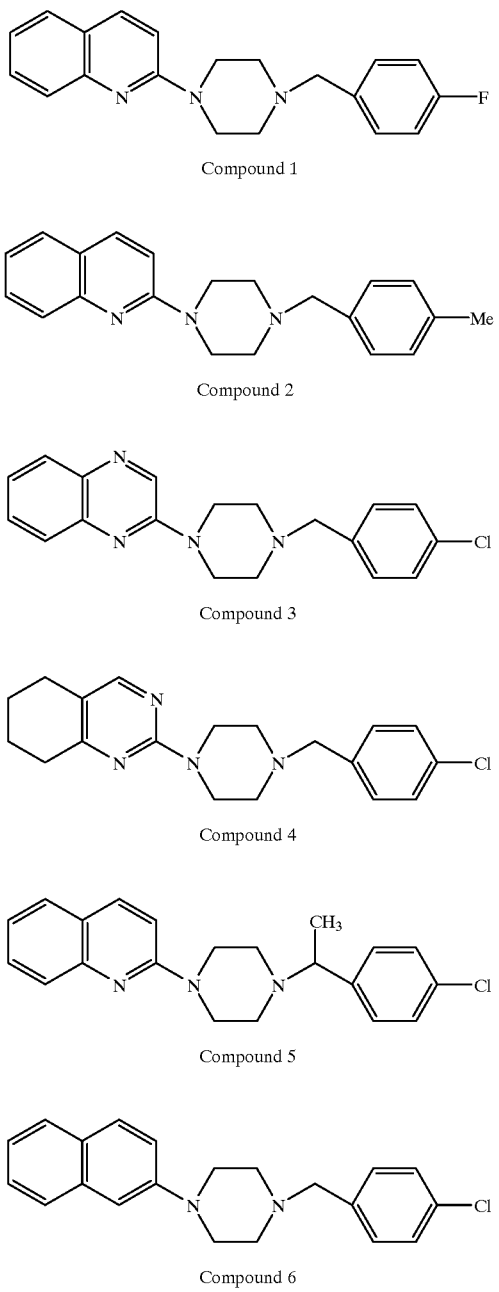

Compound 1

Compound 2

Compound 3

Compound 4

Compound 5

Compound 6

TABLE 1-continued

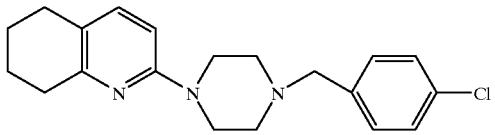

Compound 7

The compounds of the invention are useful in the treatment of neuropsychological disorders; the pharmaceutical utility of compounds of this invention is indicated by the assays for dopamine receptor subtype affinity described below in the Examples. The interaction of the 1-(2-naphthyl) and 1-(2-azanaphthyl)-4-(1-phenylmethyl)-piperazines of the invention with dopamine receptor subtypes results in the pharmacological activities of these compounds.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Representative illustrations of methods suitable for the preparation of compounds of the present invention are shown in the following Schemes. Those having skill in the art will recognize that the starting materials may be varied and additional steps employed to produce compounds encompassed by the present invention. For example, in certain situations, protection of reactive moieties such as amino groups, will be required.

An azanaphthyl compound of Formula I may be prepared according to Scheme 1.

Scheme 1

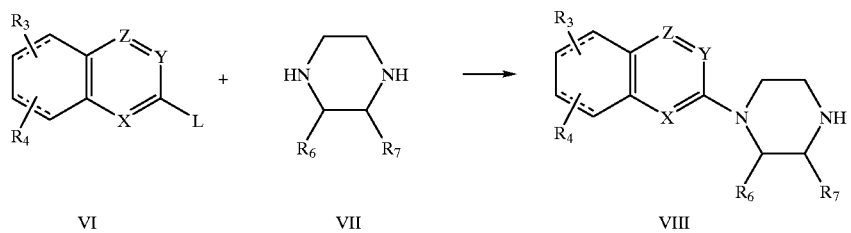

VI             VII            VIII

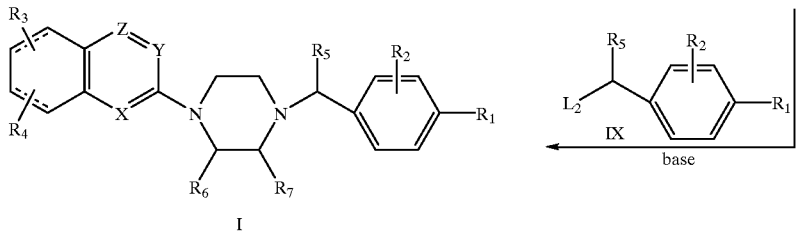

In Scheme 1, $R_1$, $R_2$, $R_3$, $R_4$, $R_5$, $R_6$, $R_7$, X, Y and Z are as defined above for Formula I.

As shown, an azanaphthyl compound of general structure VI, having an appropriate leaving group L at the position indicated, is condensed with a piperazine compound of general structure VII to provide a 1-azanaphthyl piperazine of general structure VIII. Compound VIII may then be condensed with a benzylic compound of general structure IX having an appropriate benzylic leaving group $L_2$ to provide a 1-azanaphthyl-4-(1-phenylmethyl)piperazine of Formula I. The leaving groups L and $L_2$ may be halides, sulfonate esters or the like. Those having skill in the art will recognize that the starting materials may be varied and additional steps employed to produce compounds encompassed by the present invention.

Alternatively, an azanaphthyl compound of the invention may be prepared according to Scheme 2.

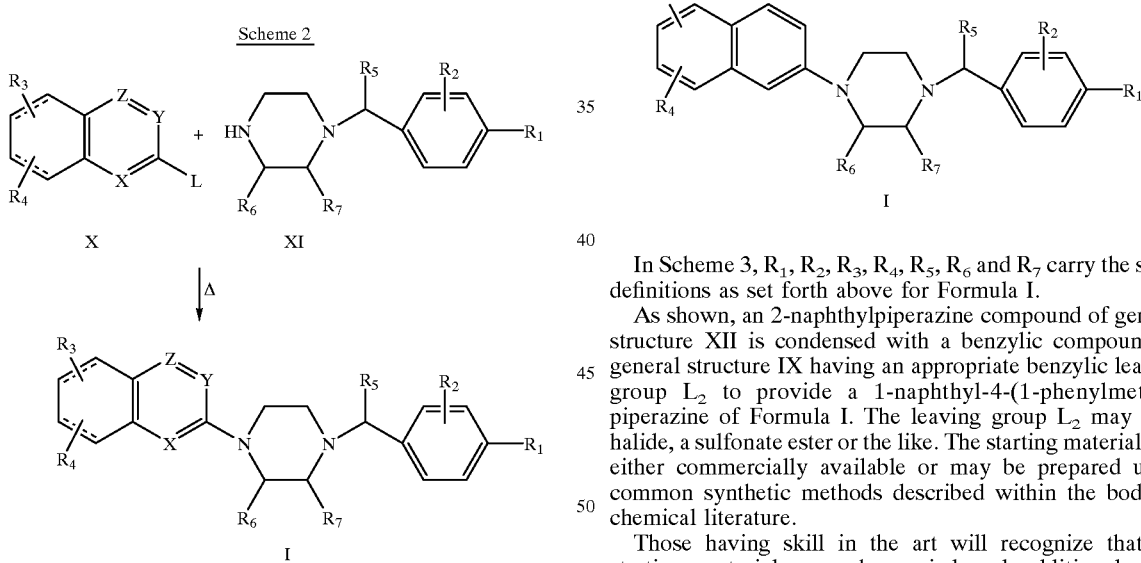

In Scheme 2, $R_1$, $R_2$, $R_3$, $R_4$, $R_5$, $R_6$, $R_7$, X, Y and Z are as defined above for Formula I.

As shown, an azanaphthyl compound of general structure X, having an appropriate leaving group L at the position indicated, is condensed with a 1-substituted piperazine compound of general structure XI to provide a 1-azanaphthyl-4-(1-phenylmethyl)piperazine of Formula I. The leaving group L may be a halide, sulfonate ester or the like. Those having skill in the art will recognize that the starting materials may be varied and additional steps employed to produce compounds encompassed by the present invention.

Naphthyl compounds of the invention may be prepared according to Scheme 3.

In Scheme 3, $R_1$, $R_2$, $R_3$, $R_4$, $R_5$, $R_6$ and $R_7$ carry the same definitions as set forth above for Formula I.

As shown, an 2-naphthylpiperazine compound of general structure XII is condensed with a benzylic compound of general structure IX having an appropriate benzylic leaving group $L_2$ to provide a 1-naphthyl-4-(1-phenylmethyl) piperazine of Formula I. The leaving group $L_2$ may be a halide, a sulfonate ester or the like. The starting materials are either commercially available or may be prepared using common synthetic methods described within the body of chemical literature.

Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, the need for such protecting groups will be apparent to those skilled in the art of organic synthesis as well as the conditions necessary to attach and remove such groups.

The disclosures in this application of all articles and references, including patents, are incorporated herein by reference.

The invention is illustrated further by the following examples which are not to be construed as limiting the invention in scope or spirit to the specific procedures described in them.

EXAMPLE 1

1. 2,4-Dichloroquinazoline

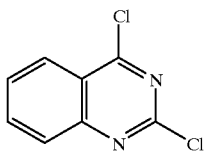

A solution of 25 g of benzoyleneurea and 12 mL of diethyl aniline in 200 mL of phosphorus oxychloride is refluxed for 4 days after which excess phosphorus oxychloride is removed on a rotovap and the remaining residue poured onto ice. The mixture is then extracted with ethyl acetate and the combined organic extracts washed with water, 1 N NaOH solution, dried and concentrated. The residue is recrystalized from isopropanol to provide 11 g of the dichloroquinazoline as off-white needles (m.p. 64–66° C.).

2. 2-Chloroquinazoline

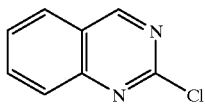

A two-phase mixture of a solution of 2, 4-dichloroquinazoline (5 g) in methylene chloride (100 mL) covered with 100 mL of saturated brine containing 9% $NH_4OH$ is treated with powdered zinc (5 g) and the resultant mixture is then refluxed for 4 h, cooled and filtered through celite. The organic layer is removed, diluted with ethyl acetate (100 ml), washed with 1 N HCl solution, dried and concentrated.

3. 2-Piperazinylquinazoline

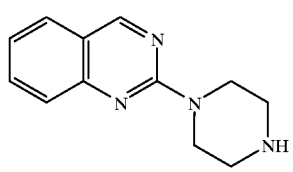

A solution of 2-chloroquinazoline (5 g) in 20 mL of toluene is added dropwise to a refluxing solution of piperazine (20 g) in 150 mL of toluene and the resultant solution refluxed for an additional 24 h. After cooling to 0° C. for 0.5 h, the solution is filtered and the filtrate extracted with 10% acetic acid. The aqueous extracts are washed with ether, basified and extracted with toluene. The toluene layer is then washed with water, dried and concentrated. Finally, the material is placed under vacuum overnight (6.8 g, m.p. 188–121° C.).

4. 2-(4-((4-chlorophenyl)methyl)piperazinyl)quinazoline

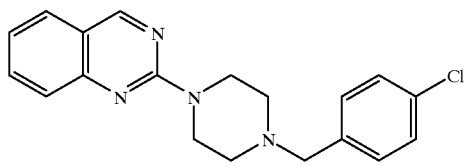

A solution of 1-quinazolin-2-ylpiperazine (250 mg, 1.2 mmol) and 4-chlorobenzyl bromide (220 mg) in acetonitrile (10 mL) containing potassium carbonate (500 mg) is stirrred and heated at 60° C. for 4 h. After cooling the reaction is partitioned between ether and water and the organic layer extracted with 1 N HCl. The acidic extract is then basified, extracted with chloroform and the organic layer is dried and concentrated to provide the product, which may alternatively be named 1-(quinazolin-2-yl)-4-(1-[4-chlorophenyl]methyl) piperazine hydrochloride, as a colorless oil (310 mg, 87%). The oxalate salt is prepared in isopropanol. $^1$H NMR (DMSO) 9.2 (s, 1H), 7.82 (d, J=4 Hz, 1H), 7.72 (T, 1H), 7.25–7.5 (m, 6H), 3.9 (m, 4H), 3.75 (s, 2H), 2.75 (m, 4H).

EXAMPLE 2

1. 2-Piperazinylquinoxaline

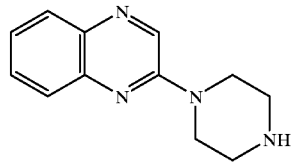

2-Hydroxyquinoxaline (1.5 g) is heated in phosphorus oxychloride (10 mL) for 12 h.after which the reaction is concentrated and the residue partitioned between methylene chloride and 1 N NaOH. The resulting crude chloride is taken up in toluene (10 mL) and this solution is then added dropwise to a refluxing solution of piperazine (5 g) in toluene (40 mL). The resulting solution is refluxed for an additional 24 h, cooled to 0° C. for 0.5 h, filtered and concentrated. The filtrate is extracted with 10% acetic acid and the aqueous extracts washed with ether, basified and extracted with toluene. The toluene layer is washed with water, dried and concentrated. The concentrated material, which may alternatively be named quinoxalin-2-ylpiperazine, is placed under vacuum overnight (1.2 g, 77%, m.p. 74–76° C.). $^1$H NMR (CDCl$_3$) 8.6 (s, 1H), 7.87 (dd, J=8, 1 Hz, 1H), 7.68 (dd, J=8, 1 Hz, 1H), 7.57 (ddd, J=8, 7, 1 Hz, 1H), 7.39 (ddd, J=8, 7, 1 Hz, 1H), 3.76 (t, J=5 Hz, 4H), 3.02 (t, J=5 Hz, 4H).

2. 1-(Quinoxalin-2-yl)-4-(1-[4-methylphenyl]methyl) piperazine oxalate

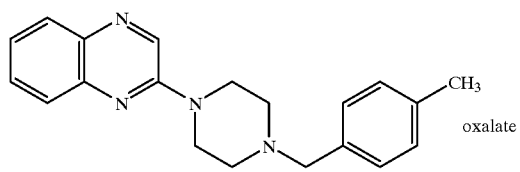

A solution of quinoxalin-2-ylpiperazine (325 mg, 1.53 mmol) and 4-methylbenzyl bromide (340 mg) in acetonitrile (10 mL) containing potassium carbonate (500 mg) is stirrred and heated at 60° C. for 4 h. After cooling, the reaction is partitioned between ether and water and the organic layer extracted with 1 N HCl. The acidic extract is then basified and extracted with chloroform. The organic layer is dried and concentrated to provide the product as a colorless oil (320 mg, 66%). The oxalate salt is prepared in isopropanol.

EXAMPLE 3

The following compounds are prepared essentially according to the procedures set forth above in Examples 1 and 2:

(a) 1-(quinazolin-2-yl)-4-(1-[4-chlorophenyl]-methyl) piperazine oxalate (m.p. 207–209° C.)

(b) 1-(quinoxalin-2-yl)-4-(1-[4-chlorophenyl]-methyl) piperazine oxalate (m.p. 209–212° C.)

(c) 1-(3-methylquinoxalin-2-yl)-4-(1-[4-chlorophenyl]-methyl)piperazine hydrobromide (m.p. 293–295° C.)

(d) 1-(quinolin-2-yl)-4-(1-[4-methylphenyl]-methyl)piperazine hydrochloride (m.p. 278–280° C.)

(e) 1-(quinolin-2-yl)-4-(1-[4-ethylphenyl]methyl)piperazine (f) 1-(quinolin-2-yl)-4-(1-[4-isopropylphenyl]-methyl)piperazine hydrochloride (m.p. 270–271° C.)

(g) 1-(quinolin-2-yl)-4-(1-[4-tert-butylphenyl]-methyl)piperazine hydrochloride (m.p. 285–287° C.)

(h) 1-(quinolin-2-yl)-4-(1-[4-fluorophenyl]-methyl)piperazine (i) 1-(quinolin-2-yl)-4-(1-[4-chlorophenyl]-methyl)piperazine hydrobromide (m.p. 268–271° C.)

(j) 1-(quinolin-2-yl)-4-(1-[3,4-dichlorophenyl]-methyl)piperazine hydrobromide (m.p. 285–287° C.)

(k) 1-(quinolin-2-yl)-4-(1-[4-trifluoromethylphenyl]-methyl)piperazine hydrobromide (m.p. 271–273° C.)

(l) 1-(quinolin-2-yl)-4-(1-[4-trifluoromethoxyphenyl]-methyl)piperazine (m.p. 109–110° C.)

(m) 1-(quinolin-2-yl)-4-(1-[3,4-methylenedioxyphenyl]-methyl)piperazine hydrobromide (m.p. 279–280° C.)

(n) 1-(4-methylquinolin-2-yl)-4-(1-[4-chlorophenyl]-methyl)piperazine hydrobromide (m.p. 215–217° C.)

(o) 1-(4,6-dimethylquinolin-2-yl)-4-(1-[4-chlorophenyl]-methyl)piperazine hydrobromide (p) 1-(4,7-dimethylquinolin-2-yl)-4-(1-[4-chlorophenyl]-methyl)piperazine hydrobromide (m.p. 295–296° C.)

(q) 1-(4,8-dimethylquinolin-2-yl)-4-(1-[4-chlorophenyl]-methyl)piperazine hydrobromide (m.p. 262–264° C.)

(r) 1-(quinolin-2-yl)-4-(1-[4-chlorophenyl]ethyl)piperazine hydrobromide (m.p. 285–287° C.)

(s) 1-(4-fluoroquinolin-2-yl)-4-(phenylmethyl)piperazine oxalate (m.p. 186–187° C.)

(t) 1-(4-fluoroquinolin-2-yl)-4-(1-[4-fluorophenyl]-methyl)piperazine oxalate (m.p. 191–193° C.)

EXAMPLE 4

1. 2, 4-Dichloro-5,6,7,8-tetrahydroauinazoline

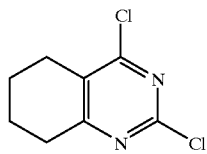

Dihydroxyquinazoline (10 g) is dissolved in phosphorus oxychloride (100 mL) and diethyl aniline (15 g). The resulting dark solutuion is brought to reflux for 24 h, cooled and concentrated. The residue is taken up in chloroform, washed with ice cold 1N NaOH solution, dried and concentrated. The resulting solid is recrystallized from ethyl acetate to provide the dichloro compound (9.2 g, 76%.

2. 2-Chloro-5,6,7,8-tetrahydroguinazoline

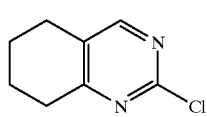

2, 4-Dichloro-5,6,7,8-tetrahydroquinazoline (4 g) is dissolved in 50 mL of methylene chloride and the resulting solution covered with 9% NH$_4$OH in saturated brine. Zinc (4 g) is added and the resulting mixture gently refluxed overnight. After filtration through celite, the organic layer is washed with water, dried and concentrated.

3. 1-(5,6,7,8-tetrahydroquinazolin-2-yl)-4-(1-[4-chlorophenyl]methyl) piperazine oxalate

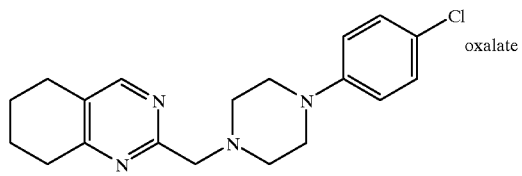

A solution of 1 g of 2-hydroxy-5,6,7,8-tetrahydroquinazoline and 0.1 g of diethylaniline in 10 mL of phosphorus oxychloride is refluxed for 2 h, and subsequently cooled and concentrated. The residue is taken up in chloroform and washed with excess 3 N NaOH solution. The organic layer is dried and concentrated to provide 2-chloro-5,6,7,8-tetrahydroquinazoline (1.1 g) as an orange solid.

A portion of this material (200 mg, 1.2 mmol) is mixed neat with an equivalent amount of 1-(4-chlorobenzyl)piperazine (250 mg) and the resultant mixture is heated to 150° C. under nitrogen for 30 min. Upon cooling, the resulting homogenous mixture is partitoned between chloroform and 10% NH$_4$OH solution. The organic layer is dried and concentrated. The residue is then taken up in hot isopropanol (3 mL) and treated with oxalic acid (108 mg) in a minimum amount of hot isopropanol to provide the desired product, which may also be named as 2-((4-(4-chlorophenyl)-piperazinyl)methyl)-5,6,7,8-tetrahydroquinazoline, oxalic acid salt, as an off-white solid (213 mg, 41%, m.p. 210–212° C.).

EXAMPLE 4

1-(5,6,7,8-tetrahydroquinolin-2-yl)-4-(1-[4-chlorophenyl] methyl) piperazine hydrobromide

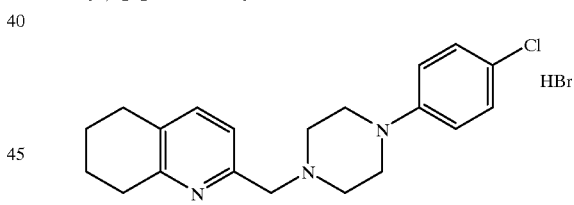

A solution of 0.7 g of 2-hydroxy-5,6,7,8-tetrahydroquinoline (prepared according to the methods outlined by Meyers et al., J. Org. Chem., 29: 1435–1438, 1964) and 0.1 g of diethylaniline in 7 mL of phosphorus oxychloride is refluxed for 2 h, cooled and concentrated. The residue taken is up in chloroform, washed with excess 3 N NaOH solution and the organic layer dried and concentrated to provide crude 2-chloro-5,6,7,8-tetrahydro-quinoline (0.45 g) as an oil.

A portion of this material (150 mg, 0.9 mmol)is mixed neat with an equivalent amount of 1-(4-chlorobenzyl) piperazine (189 mg) and the resultant mixture heated to 150° C. under nitrogen for 20 min. Upon cooling, the resulting homogenous mixture is triturated with isopropanol to provide the desired product, which may alternatively be named as 4-(4-chlorophenyl)-1-(2-5,6,7,8-tetrahydroquinolylmethyl)piperazine, hydrobromide salt, as an off-white solid (274 mg, 81%, m.p. 281–283° C.). $^1$H NMR (CDCl$_3$) 7.31 (s, 4H), 7.18 (d, J=4 Hz, 1H), 6.42 (d, J=4 Hz, 1H), 3.56 (s, 2H), 3.52 (m, 4H), 2.75 (m, 2H), 2.6 (m, 6H), 1.7–1.85 (m, 4H).

The following compound is prepared essentially according to the procedures set forth above in Examples 3 and 4:

(a) 1-(6-methoxy-4-methylquinolin-2-yl)-4-(1-[4-chlorophenyl]methyl)piperazine hydrochloride (m.p. 250–253° C.)

EXAMPLE 5
1-(Naphth-2-yl) piperazine

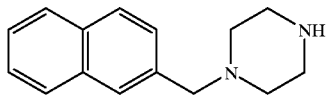

A mixture of phosphorus pentoxide (17 g) and triethyl amine hydrochloride (16.5 g) is heated and stirred under nitrogen until melted (240° C.). To this mixture is then added 2-aminonaphthalene (5.72 g) and diethanolamine (4.2 g), and the temperature maintained for 0.5 h. After cooling to approx. 100° C., the mixture is poured onto ice, neutralized with 1N NaOH, and extracted with chloroform. The organic layer is washed with water, dried and concentrated. The hydrochloride salt is prepared in ethanol (8.1 g, m.p. 265–266° C.)

2. 1-(Naphth-2-yl)-4-(1-[4-methylphenyl]methyl-piperazine hydrochloride

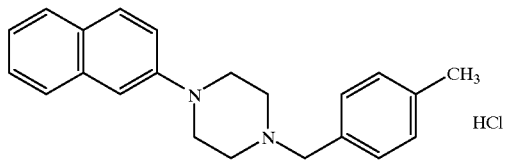

A solution of 1-(naphth-2-yl)piperazine (212 mg, 1 mmol) and 4-methylbenzyl bromide (185 mg, 1 mmol) in acetonitrile (10 mL) over potassium carbonate (500 mg) is stirred for 48 h. After partitioning between ether and water, the organic layer is extracted with 1N HCl solution, and the acidic layer is then neutralized with 6 N sodium hydroxide and extracted with chloroform. The combined chloroform extracts are dried over sodium sulfate and concentrated. The resulting oil is taken up in isopropanol and treated with a saturated solution of HCl (g) in ethyl acetate to provide the product as a white crystalline solid (374 mg, 86%).

EXAMPLE 6

The following compounds are prepared essentially according to the procedures set forth above in Example 5:

(a) 1-(naphth-2-yl)-4-(1-[4-chlorophenyl]methyl)piperazine hydrochloride (m.p. 216–218° C.)

(b) 1-(naphth-2-yl)-4-(1-[4-methylphenyl]methyl)piperazine hydrobromide (m.p. 222–223° C.)

(c) 1-(naphth-2-yl)-4-(1-[4-fluorophenyl]methyl)piperazine hydrobromide (m.p. 244–246° C.)

(d) 1-(naphth-2-yl)-4-(1-[3-fluorophenyl]methyl)piperazine hydrobromide (m.p. 253–255° C.)

(e) 1-(naphth-2-yl)-4-(1-[2-fluorophenyl]methyl)piperazine hydrobromide (m.p. 239–240° C.)

EXAMPLE 7
Assay for $D_2$ and $D_4$ Receptor Binding Activity

The pharmaceutical utility of compounds of this invention is indicated by the assays for dopamine receptor subtype affinity described below.

Pellets of COS cells containing recombinantly produced $D_2$ or $D_4$ receptors from African Green monkey are used for the assays. The sample is homogenized in 100 volumes (w/vol) of 0.05 M Tris HCl buffer at 4° C. and pH 7.4. The sample is then centrifuged at 30,000×g and resuspended and rehomogenized. The sample is again centrifuged as described above and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM $^3$H-YM 09151-2 (Nemonapride, cis-5-Chloro-2-methoxy-4-(methylamino)-N-(2-methyl-2-(phenylmethyl)-3-pyrrolidinyl)benzamide)and the compound of interest in a total incubation of 1.0 ml. Nonspecific binding is defined as that binding found in the presence of 1 mM spiperone; without further additions, nonspecific binding is less than 20% of total binding. Binding characteristics for examples of compounds encompassed within Formula I for the $D_2$ and $D_4$ receptor subtypes are shown in Table 2 for rat striatal homogenates.

TABLE 2

Binding of compounds of the invention to $D_4$ and $D_2$ receptors cloned from African Green monkey.

| Compound Number | $D_4$ $K_i$ (nM) | $D_2$ $K_i$ (nM) |
|---|---|---|
| 2 | 8 | >4000 |
| 3 | 11 | >4000 |
| 6 | 9 | >4000 |
| 7 | 7 | 1927 |

Compound numbers in Table 2 relate to compounds shown in Table 1.

The binding characteristics of compounds of Formula I for the $D_4$ receptor, expressed in nM, generally range from about 0.5 nanomolar (nM) to about 25 nanomolar (nM). These compounds typically have binding constants for the $D_2$ receptor of from about 200 nM to more than 1000 nM. Thus, the compounds of the invention are generally at least about 10 time more selective for the $D_4$ receptor than the $D_2$ receptor. Preferably, these compounds are at least 20, and more preferably at least 25–50, times more selective for the $D_4$ receptor than the $D_2$ receptor. Most preferably, these compounds are at least 100 times more selective for the $D_4$ receptor than the $D_2$ receptor.

EXAMPLE 8

A compound described in Arch. Med. Res. 25: 435–440 (Terron et al., 1994), 1-(quinolin-2-yl)-4-benzylpiperazine (Comparative Compound B), was evaluated in the assays described above. Comparative Compound B demonstrated relatively weak interaction with the $D_4$ receptor subtype ($IC_{50}$=194 nM).

A compound described in Toxicol. Appl. Pharmacol., 7: 257–267 (Schmidt and Martin, 1965), 1-naphth-2-yl-4-benzylpiperazine (Comparative Compound A), was evaluated in the assays described above. Comparative Compound A demonstrated relatively weak interaction with the $D_4$ receptor subtype ($IC_{50}$=33 nM).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made

What is claimed is:

1. A compound of the formula:

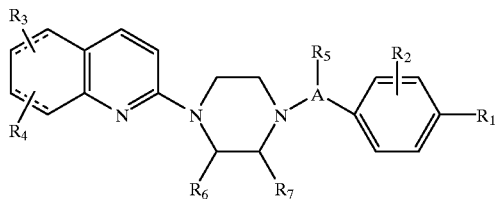

or the pharmaceutically acceptable addition salts thereof, wherein:

$R_1$ and $R_2$ independently represent hydrogen, fluoro, chloro, bromo, $C_2$–$C_6$ alkyl, trifluoromethyl, trifluoromethoxy or $SO_2NH_2$, provided that at least one of $R_1$ and $R_2$ is not hydrogen;

$R_3$ and $R_4$ are the same or different and represent hydrogen, halogen, $C_1$–$C_6$ alkyl, $C_1$–$C_4$ alkoxy, alkylthio, hydroxy, amino, mono or dialkyl amino where each alkyl is $C_1$–$C_6$ alkyl, cyano or trifluoromethyl; and $R_5$, $R_6$, and $R_7$ are the same or different and represent hydrogen or $C_1$–$C_6$ alkyl.

2. A compound according to claim 1, wherein

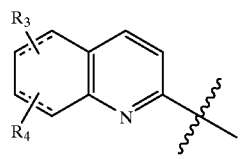

represents 4-alkylquinolinyl, 4,6-dialkylquinolinyl, 4,7-dialkylquinolinyl, 4,8-dialkylquinolinyl, 4-haloquinolinyl, or 4-alkyl-6-alkoxyquinolinyl.

3. A compound according to claim 1, which is 1-(quinolin-2-yl)-4-(1-[4-ethylphenyl]methyl)piperazine.

4. A compound according to claim 1, which is 1-(quinolin-2-yl)-4-(1-[4-tert-butylphenyl]methyl)piperazine.

5. A compound according to claim 1, which is 1-(quinolin-2-yl)-4-(1-[4-fluorophenyl]methyl)piperazine.

6. A compound according to claim 1, which is 1-(quinolin-2-yl)-4-(1-[4-chlorophenyl]methyl)piperazine.

7. A compound according to claim 1, which is 1-(quinolin-2-yl)-4-(1-[3,4-dichlorophenyl]methyl)piperazine.

8. A compound according to claim 1, which is 1-(quinolin-2-yl)-4-(1-[4-trifluoromethylphenyl]methyl)piperazine.

9. A compound according to claim 1, which is 1-(quinolin-2-yl)-4-(1-[4-trifluoromethoxyphenyl]methyl)piperazine.

10. A compound according to claim 1, which is 1-(quinolin-2-yl)-4-(1-[4-sulfonamidophenyl]methyl)piperazine.

11. A compound according to claim 1, which is 1-(5,6,7,8-tetrahydroquinolin-2-yl)-4-(1-[4-chlorophenyl]methyl)piperazine.

12. A compound according to claim 2, which is 1-(4-methylquinolin-2-yl)-4-(1-[4-chlorophenyl]methyl)piperazine.

13. A compound according to claim 2, which is 1-(4,6-dimethylquinolin-2-yl)-4-(1-[4-chlorophenyl]methyl)piperazine.

14. A compound according to claim 2, which is 1-(4,7-dimethylquinolin-2-yl)-4-(1-[4-chlorophenyl]methyl)piperazine.

15. A compound according to claim 2, which is 1-(4,8-dimethylquinolin-2-yl)-4-(1-[4-chlorophenyl]methyl)piperazine.

16. A compound according to claim 2, which is 1-(6-methoxy-4-methylquinolin-2-yl)-4-(1-[4-chlorophenyl]methyl)piperazine.

17. A compound according to claim 1, which is 1-(quinolin-2-yl)-4-(1-[4-chlorophenyl]ethyl)piperazine.

18. A compound according to claim 2, which is 1-(4-fluoroquinolin-2-yl)-4-(1-phenylmethyl)piperazine.

19. A compound according to claim 2, which is 1-(4-fluoroquinolin-2-yl)-4-(1-[4-fluorophenyl]methyl)piperazine.

20. A compound according to claim 1, wherein

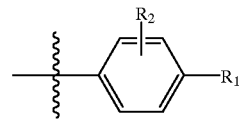

represents a group of the formula

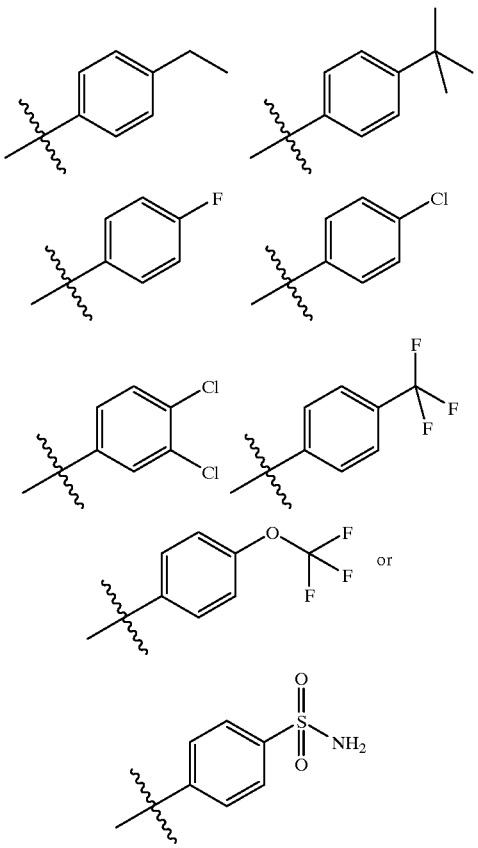

21. A compound according to claim 20, wherein at least one of $R_1$ and $R_2$ is chloro, fluoro, ethyl, butyl, isopropyl, n-propyl, trifluoromethyl, or trifluoromethoxy.

22. A compound according to claim 2, wherein
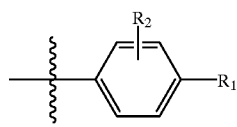
represents a group of the formula
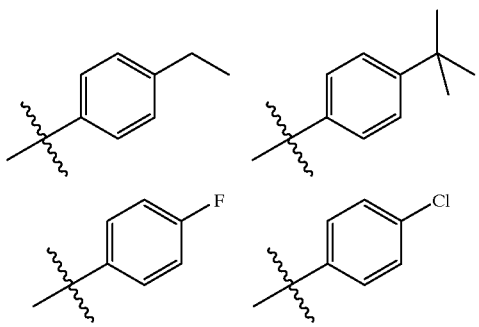
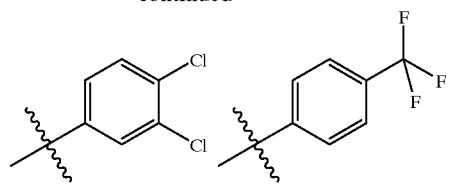
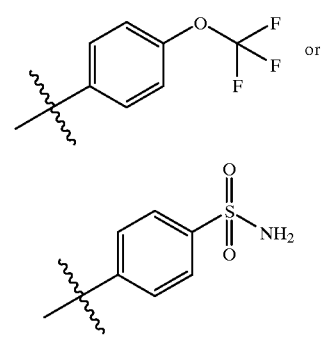
23. A compound according to claim 1, wherein at least one of $R_1$ and $R_2$ is chloro, fluoro, ethyl, butyl, isopropyl, n-propyl, trifluoromethyl, or trifluoromethoxy.
* * * * *